(12) United States Patent
Miyata et al.

(10) Patent No.: US 9,492,642 B2
(45) Date of Patent: Nov. 15, 2016

(54) GUIDEWIRE

(71) Applicant: ASAHI INTECC CO., LTD., Nagoya-shi, Aichi (JP)

(72) Inventors: Naohiko Miyata, Nagoya (JP); Muneya Furukawa, Seto (JP)

(73) Assignee: ASAHI INTECC CO., LTD., Nagoya (JP)

( * ) Notice: Subject to any disclaimer, the term of this patent is extended or adjusted under 35 U.S.C. 154(b) by 165 days.

(21) Appl. No.: 14/310,437

(22) Filed: Jun. 20, 2014

(65) Prior Publication Data
US 2015/0157830 A1 Jun. 11, 2015

(30) Foreign Application Priority Data
Dec. 6, 2013 (JP) ................. 2013-252887

(51) Int. Cl.
*A61B 5/00* (2006.01)
*A61M 25/09* (2006.01)

(52) U.S. Cl.
CPC .... *A61M 25/09* (2013.01); *A61M 2025/09083* (2013.01); *A61M 2025/09108* (2013.01); *A61M 2025/09191* (2013.01)

(58) Field of Classification Search
CPC ......... A61M 25/09; A61M 25/09016; A61M 2025/09083; A61M 2025/09108; A61M 2025/09191
See application file for complete search history.

(56) References Cited

U.S. PATENT DOCUMENTS

| 5,299,580 | A | 4/1994 | Atkinson et al. |
| 5,313,967 | A | 5/1994 | Lieber et al. |
| 6,059,771 | A | 5/2000 | Balbierz et al. |
| 8,113,916 | B2 | 2/2012 | Miller et al. |
| 8,845,553 | B2 * | 9/2014 | Brown ............... A61M 25/09 600/585 |
| 2002/0043118 | A1 | 4/2002 | Claude |
| 2004/0142643 | A1 | 7/2004 | Miller et al. |
| 2004/0215109 | A1 | 10/2004 | Pingleton et al. |
| 2013/0304108 | A1 | 11/2013 | Weber et al. |
| 2014/0103273 | A1 | 4/2014 | Nakajima et al. |
| 2015/0094691 | A1 | 4/2015 | Miyata et al. |
| 2015/0094692 | A1 | 4/2015 | Miyata et al. |

FOREIGN PATENT DOCUMENTS

| EP | 0 826 389 A2 | 3/1998 |
| EP | 2 163 276 A1 | 3/2010 |
| JP | 10216236 | 8/1998 |
| JP | 2008-155054 A | 7/2008 |
| JP | 2011-125556 A | 6/2011 |

(Continued)

OTHER PUBLICATIONS

Mar. 6, 2015 Search Report issued in European Search Report Application No. 14173746.0.

(Continued)

*Primary Examiner* — Max Hindenburg
(74) *Attorney, Agent, or Firm* — Oliff PLC

(57) ABSTRACT

A guidewire suppresses an increase in operating resistance during pushing and pulling within a blood vessel that is extremely crooked and secures sufficient operability. The guidewire includes a core shaft and a coil body wound around the core shaft. The core shaft includes a first shaft portion positioned inside the coil body and a second shaft portion positioned proximally from the coil body. A twisted portion that is twisted along a longitudinal axis of the core shaft is provided in at least part of the second shaft portion.

10 Claims, 3 Drawing Sheets

(56) References Cited

FOREIGN PATENT DOCUMENTS

| | | |
|---|---|---|
| JP | A-2012-070906 | 4/2012 |
| JP | 2013-85781 A | 5/2013 |
| JP | 201570895 A | 4/2015 |
| JP | 201570896 A | 4/2015 |
| WO | WO 2012/172881 A1 | 12/2012 |

OTHER PUBLICATIONS

Mar. 12, 2015 Search Report issued in European Search Report Application No. 14173744.5.
U.S. Appl. No. 14/315,990, filed Jun. 26, 2014.
U.S. Appl. No. 14/316,229, filed Jun. 26, 2014.
Nov. 17, 2015 Office Action issued in Japanese Patent Application No. 2013-207156.
Written Directive issued in Japanese Patent Application No. 2013-207156.
Nov. 17, 2015 Office Action issued in Japanese Patent Application No. 2013-207162.
Written Directive issued in Japanese Patent Application No. 2013-207162.
Nov. 9, 2015 Office Action issued in Japanese Patent Application No. 2013-252887.
Sep. 11, 2014 Search Report issued in European Patent Application No. 14173742.9.
Jul. 29, 2015 Office Action issued in U.S. Appl. No. 14/316,229.
Jul. 29, 2015 Office Action issued in U.S. Appl. No. 14/315,990.
May 11, 2016 Office Action issued in Japanese Patent Application No. 2013-252887.

* cited by examiner

GUIDEWIRE

CROSS-REFERENCE TO RELATED APPLICATION

This application claims priority to Japanese Application No. 2013-252887 which was filed on Dec. 6, 2013, the entire contents of which is hereby incorporated by reference.

BACKGROUND

The disclosed embodiments relate to a medical device. Specifically, the disclosed embodiments relate to a guidewire used as a medical device which is inserted into a lumen for the purposes of treatment and inspection.

Conventionally, various devices have been proposed as a medical device that is inserted into a tubular organ, such as a blood vessel, a digestive tract, or a urinary duct, and an in-vivo tissue for the purposes of treatment and inspection.

For example, U.S. Pat. No. 5,299,580 discloses a guidewire having a shaft twisted around its longitudinal axis. In the guidewire, a twisted portion is provided in a portion of the shaft positioned inside of a coil body. On the other hand, a large-diameter portion of the shaft positioned proximally from the coil body is not twisted but has a smooth surface.

SUMMARY

For example, when one inserts a guidewire along an inverted U-shaped path extending from a blood vessel in the lower limb of the right leg to a blood vessel in the lower limb of the left leg according to a crossover method, operating resistance during pushing and pulling of the guidewire increases because the guidewire slides on a vascular wall when the guidewire passes the top portion of such an extremely crooked blood vessel. As a result, the operability may decrease.

In the guidewire disclosed in U.S. Pat. No. 5,299,580, when a large-diameter portion of the shaft positioned proximally from the coil body slides on the vascular wall, sliding resistance increases and the operability may decrease as described above. In this respect, there is room for improvement.

The disclosed embodiments have been made in view of such circumstances, and an object thereof is to provide a guidewire capable of suppressing an increase in operating resistance during pushing and pulling within a blood vessel that is extremely crooked and securing sufficient operability.

In order to solve the problems, a shaft according to an aspect of the present invention and a guidewire using the shaft have the following features.

A guidewire according to a first aspect of the present invention includes: a core shaft; and a coil body that covers the core shaft. The core shaft includes: a first shaft portion positioned inside the coil body; and a second shaft portion positioned proximally from the coil body. A twisted portion that is twisted along a longitudinal axis of the core shaft is provided in at least part of the second shaft portion.

A second aspect of the present invention is the guidewire according to the first aspect, in which the twisted portion is provided over the entire second shaft portion.

A third aspect of the present invention is the guidewire according to the first or second aspect, in which the twisted portion of the second shaft portion has a cross-section in a direction perpendicular to the longitudinal axis of the core shaft, which is formed in a substantially rectangular shape.

A fourth aspect of the present invention is the guidewire according to any one of the first to third aspects, in which the twisted portion is formed in such a tapered shape that a diameter thereof decreases as the twisted portion advances toward a distal end of the guidewire.

In the guidewire of the first aspect, the second shaft portion of the core shaft positioned proximally from the coil body is twisted along its longitudinal axis. According to this configuration, a plurality of spiral grooves is provided at a predetermined interval along the longitudinal axis in the second shaft portion positioned proximally from the coil body. Due to this, when the guidewire is inserted into a blood vessel, the plurality of spiral grooves can decrease a contact area with the vascular wall.

Therefore, even when one inserts a guidewire along an inverted U-shaped path extending from a blood vessel in the lower limb of the right leg to a blood vessel in the lower limb of the left leg according to a crossover method, for example, the movement of the guidewire is not suppressed by the sliding on the vascular wall when the guidewire passes the top portion of the path, and the distal end thereof can be smoothly inserted into a deeper portion. Further, it is possible to suppress damage of the blood vessel.

In the guidewire of the second aspect, the twisted portion is provided on the entire second shaft portion. According to this configuration, a contact area with the vascular wall when the guidewire is inserted into the blood vessel can be reduced further as compared to a configuration in which only a portion of the second shaft portion is twisted, for example.

That is, even when one inserts a guidewire along an inverted U-shaped path extending from a blood vessel in the lower limb of the right leg to a blood vessel in the lower limb of the left leg according to a crossover method, for example, the movement of the guidewire is not suppressed by the sliding on the vascular wall when the guidewire passes the top portion of the path, and the distal end thereof can be smoothly inserted into a deeper portion.

In the guidewire of the third aspect, the cross-section of the twisted portion of the second shaft portion is formed in a substantially rectangular shape. According to this configuration, the area contacting the vascular wall decreases and the load on the vascular wall during the contact decreases as compared to a configuration in which the twisted portion has an approximately circular cross-sectional shape (a configuration in which the entire outer surface makes contact with the vascular wall).

Thus, when the guidewire advances into the blood vessel while revolving, the contact resistance with respect to the vascular wall decreases. As a result, the operating resistance during pushing and pulling of the guidewire is further reduced and the operability can be improved further. Moreover, even when one inserts a guidewire along an inverted U-shaped path extending from a blood vessel in the lower limb of the right leg to a blood vessel in the lower limb of the left leg according to a crossover method, for example, the movement of the guidewire is not suppressed by the sliding on the vascular wall when the guidewire passes the top portion of the path, and the distal end thereof can be inserted into a deeper portion further smoothly.

In the guidewire of the fourth aspect, the twisted portion is formed in such a tapered shape that the diameter thereof decreases as the twisted portion advances toward the distal end. According to this configuration, the distal end portion of the twisted portion has flexibility, and even when one inserts a guidewire along an inverted U-shaped path extending from a blood vessel in the lower limb of the right leg to a blood vessel in the lower limb of the left leg according to a crossover method, for example, satisfactory followability is obtained.

Moreover, in the twisted portion having such a configuration, the depth of the spiral groove positioned on a distal side is smaller than the depth of the spiral groove positioned on a proximal side. According to this configuration, blood (liquid) is easily stored on the outer periphery of a portion (a portion where substantially no spiral groove is present, that is, the distal end portion) of the twisted portion having a relatively small diameter and having a shallow spiral groove. In this state, when the guidewire is pushed into the deeper portion, the blood (liquid) stored on the outer periphery of the small-diameter portion flows toward the large-diameter portion (a portion having a relatively deep spiral groove, that is, the base end portion), and thus, the lubricity of the surface of the twisted portion can be improved. As a result, the operability of the guidewire within the blood vessel is improved.

DETAILED DESCRIPTION OF EMBODIMENTS

Figure 1:
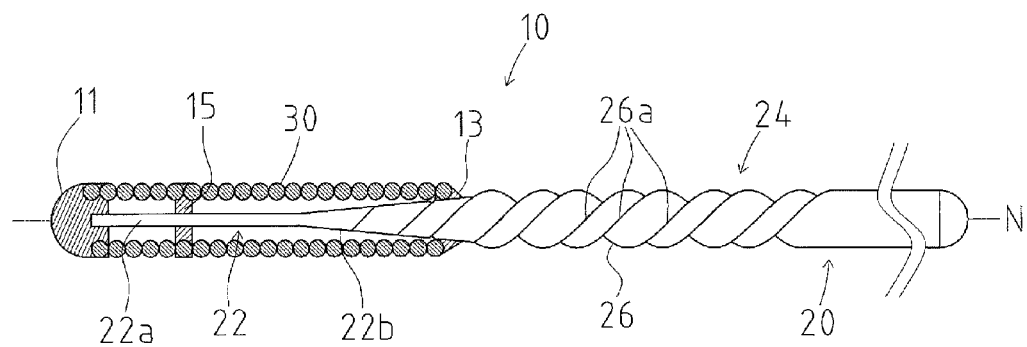
FIG. 1 is a general view illustrating an exemplary embodiment of a guidewire.

First, a shaft will be described based on preferred embodiments illustrated in the drawings.

FIG. 1 is a general view illustrating a guidewire. In FIG. 1, the left side is a distal end that is inserted into the body, and the right side is a proximal end that is operated by a surgeon such as a physician. This drawing schematically illustrates the guidewire and does not necessarily reflect an actual dimensional ratio.

A guidewire 10 illustrated in FIG. 1 is used for treatment of a blood vessel in the lower limb according to a crossover method, for example. The guidewire 10 includes a core shaft 20 and a coil body 30 that covers the outer periphery of a distal end portion of the core shaft 20.

First, the core shaft 20 will be described. The core shaft 20 includes a first shaft portion 22 positioned inside the coil body 30 and a second shaft portion 24 positioned proximally from the coil body 30.

The first shaft portion 22 includes a small-diameter portion 22a and a tapered portion 22b which are arranged in that order from the distal end to the proximal end. The small-diameter portion 22a is a portion that is the closest to the distal end of the core shaft 20 and is the most flexible portion of the core shaft 20. The small-diameter portion 22a is formed in a planar shape by pressing. The tapered portion 22b has a circular tapered cross-section and the diameter thereof decreases as the tapered portion advances toward the distal end.

The arrangement and dimensions of the small-diameter portion 22a and the tapered portion 22b can be changed appropriately for reasons such as to obtain a desired strength. For example, the small-diameter portion 22a may have a circular, columnar shape. Moreover, the number of tapered portions 22b and the angle of the tapered portion 22b may be set appropriately as necessary.

In the first shaft portion 22 of the present embodiment, the distal end portion is not twisted but has a smooth surface, and only a proximal end portion is twisted. That is, a portion of the first shaft portion 22 connected to a proximal end junction 13 described later is twisted. Due to this, the junction 13 is inserted into a spiral groove of the core shaft 20 formed by being twisted, whereby the coil body 30 can be tightly connected to the core shaft 20.

On the other hand, the second shaft portion 24 forms a portion of the core shaft 20 exposed from the coil body 30. In FIG. 1, only the distal end portion of the second shaft portion 24 is twisted, and the twisted portion 26 is formed in only the distal end portion of the second shaft portion 24. That is, portions of the second shaft portion 24 other than the twisted portion 26 do not have the spiral groove and have a smooth surface.

In the present embodiment, the distal end portion of a portion of the second shaft portion 24 exposed from the coil body 30 is twisted. Due to this, a number of spiral grooves 26a reduces the sliding resistance of the distal end portion of the shaft 20 (24) with respect to the vascular wall, and the load on the vascular wall also decreases.

That is, even when one inserts the guidewire 10 along an inverted U-shaped path extending from a blood vessel in the lower limb of the right leg to a blood vessel in the lower limb of the left leg according to a crossover method, for example, the movement of the guidewire 10 is not suppressed by the sliding on the vascular wall when the guidewire passes the top portion of the path, and the distal end thereof can be smoothly inserted into a deeper portion. Further, it is possible to suppress damage of the blood vessel.

The twisted portion 26 is not provided in the proximal end portion of the second shaft portion 24 and the spiral groove is not present. Due to this, the grasping ability of a user when grasping the proximal end portion of the shaft 20 (24) is improved, and the operability is improved.

In the guidewire 10, the cross-section of the twisted portion 26 (hereinafter referred to simply as a cross-section) in the direction perpendicular to the longitudinal axis N of the second shaft portion 24 has an substantially circular shape.

A material for forming these first and second shafts 22 and 24 is not particularly limited, and for example, stainless steel (SUS304), a superelastic alloy such as a Ni—Ti alloy, a piano wire, a cobalt-based alloy, or the like can be used.

Among these materials, the distal end portion (the first shaft portion 22) of the core shaft 20 is preferably formed of a Ni—Ti alloy from the perspective of obtaining sufficient flexibility and the ability to restore its shape from a bent state and securing the ability to follow a complexly crooked blood vessel. Moreover, the proximal end portion (the second shaft portion 24) of the core shaft 20 is preferably formed of stainless steel (SUS304) from the perspective of providing appropriate rigidity (bending rigidity and torsional rigidity) and improving the pushing ability and the torque transferring ability of the guidewire 10.

Next, the coil body 30 will be described. The coil body 30 in FIG. 1 is a single-strand coil in which an element wire is wound in a spiral form. However, the structure of the coil body 30 is not limited to this. For example, the coil body 30 may be a multi-strand coil (a stranded coil formed of a plurality of element wires).

As illustrated in FIG. 1, the distal end of the coil body 30 is fixed to the distal end of the core shaft 20 by a distal end junction 11. The proximal end of the coil body 30 is fixed to the core shaft 20 by the proximal end junction 13. Moreover, an approximately intermediate portion of the coil body 30 positioned closer to the distal end than the proximal end junction 13 and closer to the proximal end than the distal end junction 11 is fixed to the core shaft 20 by an intermediate junction 15.

A material for forming the distal end junction 11, the proximal end junction 13, and the intermediate junction 15 is not particularly limited, and for example, a metal solder such as an Sn—Pb alloy, a Pb—Ag alloy, an Sn—Ag alloy, or a Au—Sn alloy can be used.

A material for forming the coil body 30 is not particularly limited, and a radio-opaque element wire or a radio-translucent element wire can be used. A material of the radio-opaque element wire is not particularly limited, and for example, gold, platinum, tungsten, alloys containing these elements (for example, a platinum-nickel alloy), or the like can be used. Moreover, a material of the radio-translucent element wire is not particularly limited, and for example, stainless steel (SUS304, SUS316, or the like), a superelastic alloy such as a Ni—Ti alloy, a piano wire, or the like can be used.

Figure 2:
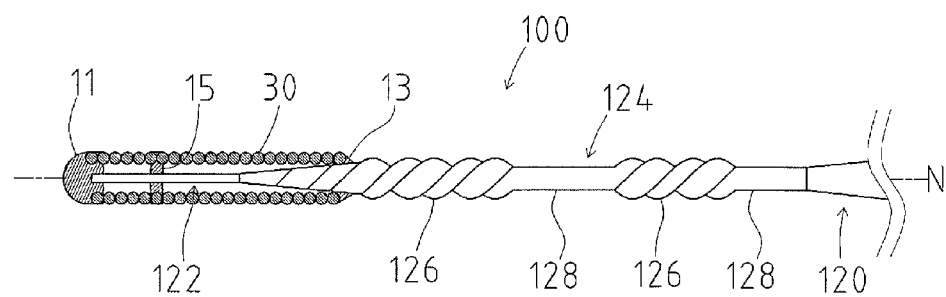
FIG. 2 is an enlarged partial detail view illustrating an exemplary embodiment of the guidewire.

Next, an exemplary embodiment of the guidewire will be described using FIG. 2. In FIG. 2, the left side is a distal end that is inserted into the body, and the right side is a proximal end that is operated by a surgeon such as a physician. This drawing schematically illustrates the guidewire and does not necessarily reflect an actual dimensional ratio.

The proximal end portion (the second shaft portion 24) of the core shaft 20 has the twisted portion 26 in its distal end portion only. In contrast, in a core shaft 120 of a guidewire 100, a plurality of twisted portions 126 is provided at a predetermined interval along the longitudinal axis of a second shaft portion 124. That is, the second shaft portion 124 includes the twisted portion 126 and a non-twisted portion 128 which are alternately provided along the longitudinal axis N.

In the second shaft portion 124 of the present embodiment having the twisted portion 126 and the non-twisted portion 128, the diameter of the non-twisted portion 128 is smaller than the diameter of the twisted portion 126. Due to this, when the guidewire 100 advances into the blood vessel while revolving, the blood (liquid) is easily stored on the outer periphery (the depressed portion) of the non-twisted portion 128. In this state, when the guidewire 100 is pushed and pulled, the blood (liquid) stored in the outer periphery (depressed portion) of the non-twisted portions 128 provided before and after the twisted portion 126 flows toward the outer periphery of the twisted portion 126, and thus, the lubricity of the surface of the twisted portion 126 can be improved. As a result, the operability of the guidewire 100 within the blood vessel is improved.

Figure 3:
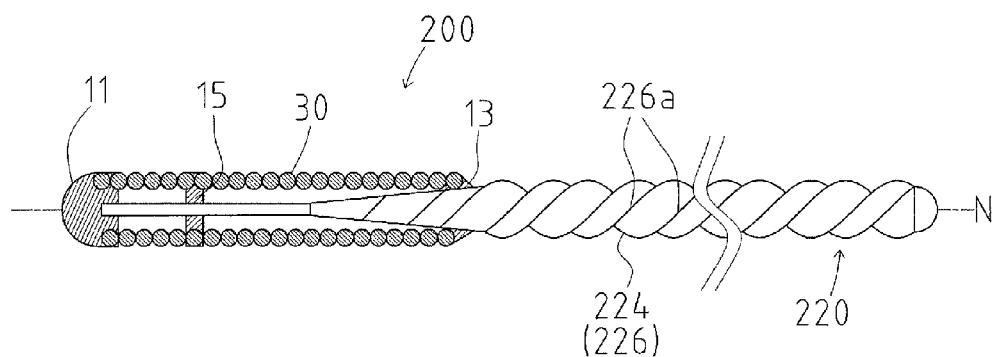
FIG. 3 is a general view illustrating an exemplary embodiment of the guidewire.

Next, an exemplary embodiment of the guidewire will be described using FIG. 3. In FIG. 3, the left side is a distal end that is inserted into the body, and the right side is a proximal end that is operated by a surgeon such as a physician. This drawing schematically illustrates the guidewire and does not necessarily reflect an actual dimensional ratio.

As described above, the proximal end portion (the second shaft portion 24, 124) of the core shaft 20, 120 is partially twisted along the longitudinal axis N. In contrast, an entirety of a base end portion (a second shaft portion 224) of a core shaft 220 of a guidewire 200 is twisted along the longitudinal axis N. That is, a twisted portion 226 is provided over the entire second shaft portion 224.

A plurality of spiral grooves 226a is provided at a predetermined interval along the longitudinal axis N over an entirety of the second shaft portion 224 positioned proximally from the coil body 30. Due to this, when the guidewire 200 is inserted into the blood vessel, the plurality of spiral grooves 226a can further reduce the contact area with the vascular wall.

That is, even when one inserts the guidewire 200 along an inverted U-shaped path extending from a blood vessel in the lower limb of the right leg to a blood vessel in the lower limb of the left leg according to a crossover method, for example, the movement of the guidewire 200 is not suppressed by the sliding on the vascular wall when the guidewire passes the top portion of the path, and the distal end thereof can be smoothly inserted into a deeper portion.

Figure 4:
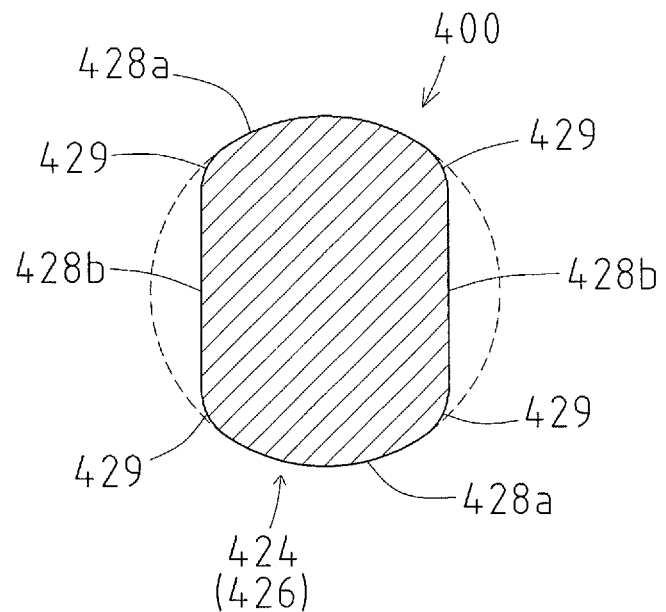
FIG. 4 is a cross-sectional view illustrating an exemplary embodiment of the guidewire.

FIG. 4 is a cross-sectional view illustrating an exemplary embodiment of the guidewire. Here, a cross-sectional shape of the twisted portion of the core shaft is different from that described above. FIG. 4 schematically illustrates the cross-section of the twisted portion of the core shaft and thus does not necessarily reflect an actual dimensional ratio.

In the guidewires described above, the cross-section of the twisted portion provided in the second shaft portion has an approximately circular shape. In contrast, in a guidewire 400, the cross-section of a twisted portion 426 has a substantially rectangular shape. That is, in a second shaft portion 424, a convex portion 428a is provided on a first pair of opposite sides of the sides forming the cross-section of the twisted portion 426, and a linear portion 428b is provided on the other sides.

According to this configuration, in the guidewire 400, the area contacting the vascular wall decreases and the load on the vascular wall during the contact decreases as compared to the guidewire in which the cross-section of the twisted portion of the second shaft portion has an approximately circular shape.

Thus, when the guidewire 400 advances into the blood vessel while revolving, the contact resistance with respect to the vascular wall decreases. As a result, the operating resistance during pushing and pulling of the guidewire 400 is reduced, the torque transferring ability is improved, and the operability is improved.

Moreover, even when one inserts the guidewire 400 along an inverted U-shaped path extending from a blood vessel in the lower limb of the right leg to a blood vessel in the lower limb of the left leg according to a crossover method, for example, the movement of the guidewire 400 is not suppressed by the sliding on the vascular wall when the guidewire passes the top portion of the path, and the distal end thereof can be smoothly inserted into a deeper portion. Further, it is possible to suppress damage of the blood vessel.

In FIG. 4, the four corners of the cross-section are preferably formed in an arc-shape to provide an arc-shaped portion 429. According to this configuration, when the guidewire 400 advances into the blood vessel while revolving, the contact resistance with respect to the vascular wall is further reduced. As a result, the operability of the guidewire 400 within the blood vessel can be improved.

Figure 5:
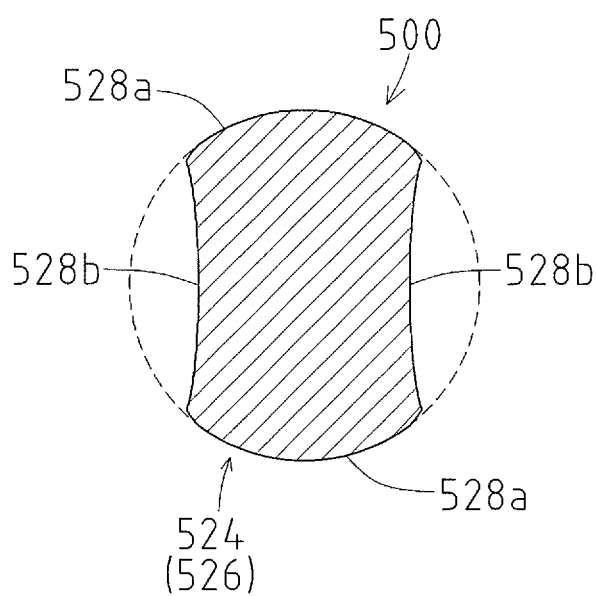
FIG. 5 is a cross-sectional view illustrating an exemplary embodiment of the guidewire.

FIG. 5 is a cross-sectional view illustrating an exemplary embodiment of the shaft. This drawing schematically illustrates the cross-section of the shaft and thus does not necessarily reflect an actual dimensional ratio.

In the guidewire 400 described above, the convex portion 428a is formed on a first pair of opposite sides of the sides forming the cross-section of the twisted portion 426, and the linear portion 428b is provided on each of the other sides other than the pair of convex portions. In contrast, in a guidewire 500, an arc-shaped concave portion 528b is provided on a second pair of opposite sides among the sides forming the cross-section of a twisted portion 526 of a second shaft portion 524.

According to this configuration, the area moment of inertia decreases as compared to a configuration having no concave portion (for example, the fourth embodiment). Due to this, even when the shaft is bent excessively in the blood vessel in the extremely crooked lower limb region in an inverted U-shape, for example, due to the load applied when contacting the vascular wall, the shaft is rarely deforms permanently. As a result, no problem may occur in the subsequent operations, and continued use of the shaft is made easy.

Figure 6:
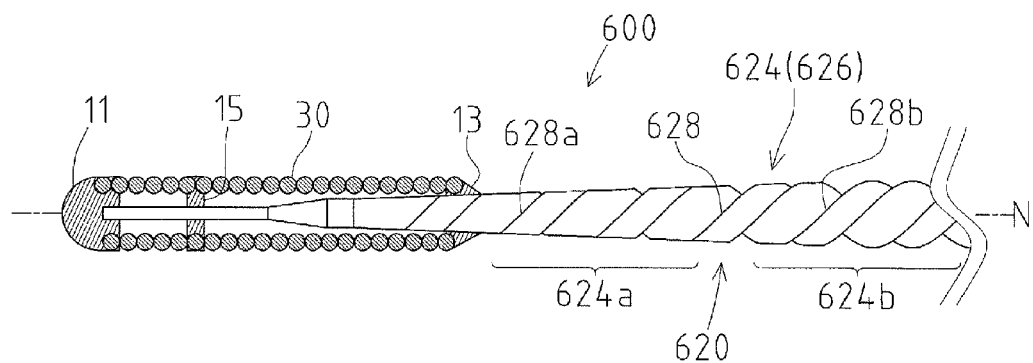
FIG. 6 is an enlarged partial detail view illustrating an exemplary embodiment of the guidewire.

Next, an exemplary embodiment of the guidewire will be described using FIG. 6. In FIG. 6, the left side is a distal end that is inserted into the body, and the right side is a proximal end that is operated by a surgeon such as a physician. This drawing schematically illustrates the guidewire and thus does not necessarily reflect an actual dimensional ratio.

A second shaft portion 624 of a core shaft 620 of a guidewire 600 of the present embodiment includes a twisted portion 626 in which an entirety of the second shaft portion is twisted along the longitudinal axis N. Moreover, the twisted portion 626 is formed in such a tapered shape that the diameter thereof decreases as the twisted portion advances toward the distal end. According to this configuration, the distal end portion of the twisted portion 626 has flexibility, and even when one inserts the guidewire 600 along an inverted U-shaped path extending from a blood vessel in the lower limb of the right leg to a blood vessel in the lower limb of the left leg according to a crossover method, for example, satisfactory followability is obtained.

Further, in the twisted portion 626 (the second shaft portion 624) having such a configuration, the depth of a spiral groove 628 decreases as the spiral groove advances toward the distal end. That is, the depth of the spiral groove 628a positioned on a distal side of the second shaft portion 624 is smaller than the depth of the spiral groove 628b positioned on proximal side of the second shaft portion 624.

According to this configuration, blood (liquid) is easily stored on the outer periphery of a portion 624a (a portion where substantially no spiral groove is present, that is, the distal end portion) of the twisted portion 626 having a relatively small diameter and having a shallow spiral groove 628. In this state, when the guidewire 600 is pushed into the deeper portion, the blood (liquid) stored on the outer periphery of the small-diameter portion 624a of the twisted portion 626 flows toward a large-diameter portion 624b (a portion having a relatively deep spiral groove 628, that is, the proximal end portion), and thus, the lubricity of the surface of the twisted portion 626 can be improved. As a result, the operability of the guidewire 600 within the blood vessel is improved.

Moreover, in general, in the proximal end portion of such a guidewire 600, a relatively large-diameter portion has larger sliding resistance with respect to the vascular wall than a relatively small-diameter portion. However, in the present embodiment, the spiral groove 628 in the large-diameter portion 624b of the second shaft portion 624 is relatively deep. Due to this, an increase in the sliding resistance with respect to the vascular wall in such a large-diameter portion 624b is suppressed.

As a result, even when the guidewire 600 is inserted into the blood vessel having an inverted U-shape present in the lower limb region, the movement of the guidewire 600 is not suppressed by the sliding of the large-diameter portion on the vascular wall when the guidewire passes the top portion of the path, and the distal end thereof can be more smoothly inserted into a deeper portion.

Figure 7:
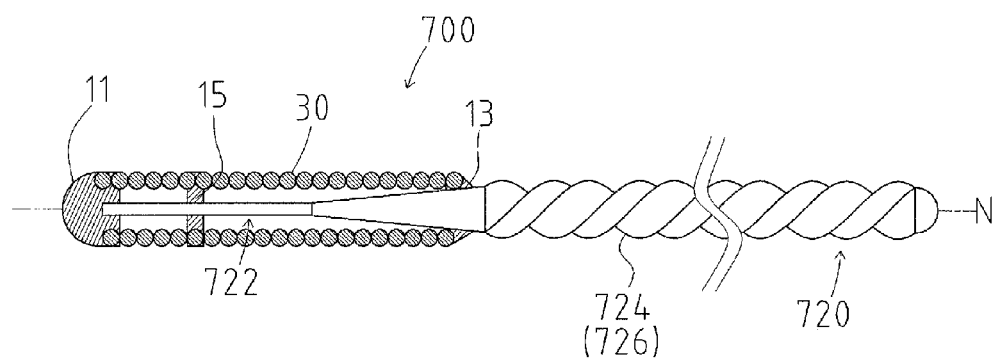
FIG. 7 is a cross-sectional view illustrating an exemplary embodiment of the guidewire.

Next, an exemplary embodiment of the guidewire will be described using FIG. 7. In FIG. 7, the left side is a distal end that is inserted into the body, and the right side is a proximal end that is operated by a surgeon such as a physician. This drawing schematically illustrates the guidewire and thus does not necessarily reflect an actual dimensional ratio.

As described above, the twisted portion is formed in the proximal end portion of the first shaft portion. In contrast, in a core shaft 720 of a guidewire 700, no twisted portion is formed in the proximal end portion of a first shaft portion 722. That is, the twisted portion 726 is formed in a second shaft portion 724 only.

For example, when the distal end portion of a guidewire is bent following the shape of a blood vessel, and the proximal end of the first shaft portion is twisted, the element wire of the coil body interferes with a spiral groove formed by the twisting so that a problem may occur when the guidewire is revolved. In FIG. 7, interference between the proximal end of the first shaft portion 722 and the coil body 30 is suppressed and satisfactory operability of the guidewire 700 can be secured.

What is claimed is:

1. A guidewire comprising:
    a core shaft; and
    a coil body that covers the core shaft, wherein
    the core shaft includes:
        a first shaft portion positioned inside the coil body; and
        a second shaft portion positioned proximally from the coil body, at least a part of the second shaft portion being provided with a twisted portion that is twisted along a longitudinal axis of the core shaft, and
        the twisted portion of the second shaft portion has a cross section that is substantially rectangular in shape and that includes convex portions on a first pair of opposite sides.

2. The guidewire according to claim 1, wherein the twisted portion is provided over an entirety of the second shaft portion.

3. The guidewire according to claim 1, wherein the cross section includes straight portions formed on a second pair of opposite sides, and arc shaped portions formed at intersections of each of the straight portions and each of the convex portions.

4. The guidewire according to claim 1, wherein the cross section includes recessed portions formed on a second pair of opposite sides.

5. The guidewire according to claim 1, wherein the twisted portion is provided on a distal end portion of the second shaft portion.

6. The guidewire according to claim 1, wherein the twisted portion is formed in a tapered shape such that a diameter of the twisted portion decreases toward a distal end of the guidewire.

7. The guidewire according to claim 1, wherein the twisted portion is formed intermittently along the second shaft portion.

8. The guidewire according to claim 7, wherein
a diameter of the second shaft portion where the twisted portion is formed is larger than a diameter of the second shaft portion where the twisted portion is not formed.
9. The guidewire according to claim 1, further comprising
a proximal end junction that joins a proximal end of the coil body to the core shaft, wherein
a proximal portion of the first shaft portion includes the twisted portion, and
the proximal end junction joins the coil body to the twisted portion.
10. The guidewire according to claim 1, wherein
the twisted portion is disposed only in the second shaft portion.

* * * * *